(12) United States Patent
Cowe et al.

(10) Patent No.: US 7,477,375 B2
(45) Date of Patent: Jan. 13, 2009

(54) OPTICAL REFERENCE STANDARD

(75) Inventors: Ian Cowe, York (GB); Arthur Springsteen, Wilmington, OH (US)

(73) Assignee: Foss Analytical AB, Hoganas (SE)

( * ) Notice: Subject to any disclaimer, the term of this patent is extended or adjusted under 35 U.S.C. 154(b) by 0 days.

(21) Appl. No.: 10/582,337

(22) PCT Filed: Dec. 7, 2004

(86) PCT No.: PCT/SE2004/001813

§ 371 (c)(1),
(2), (4) Date: May 15, 2007

(87) PCT Pub. No.: WO2005/057185

PCT Pub. Date: Jun. 23, 2005

(65) Prior Publication Data

US 2007/0289355 A1     Dec. 20, 2007

(30) Foreign Application Priority Data

Dec. 11, 2003   (SE) .................................... 0303338

(51) Int. Cl.
*G01J 1/10*     (2006.01)
(52) U.S. Cl. ................................ 356/243.1; 356/243.4
(58) Field of Classification Search ............... 356/243.1
See application file for complete search history.

(56) References Cited

U.S. PATENT DOCUMENTS

| 4,082,950 | A | * | 4/1978 | Chen .......................... 250/343 |
| 4,095,105 | A | * | 6/1978 | Rosenthal ................. 250/338.1 |
| 4,761,552 | A | | 8/1988 | Rosenthal |
| 5,459,677 | A | | 10/1995 | Kowalski et al. |

FOREIGN PATENT DOCUMENTS

| JP | 9015142 | 5/1997 |
| JP | 11101733 | 4/1999 |
| JP | 11101733 A * | 4/1999 |
| JP | 20011305055 | 10/2001 |

OTHER PUBLICATIONS

International Search Report (PCT/ISA/210).

* cited by examiner

*Primary Examiner*—Roy M Punnoose
(74) *Attorney, Agent, or Firm*—Harness, Dickey & Pierce, P.L.C.

(57) ABSTRACT

An optical reference is disclosed for wet foodstuffs including an optical reference material including a binder and a cereal formed into a matrix to fixedly hold an amount of water. The reference material is constituted with the binder, the cereal and the water present in amounts to provide the reference standard with desired spectral, mechanical and temporal characteristics.

5 Claims, 3 Drawing Sheets

OPTICAL REFERENCE STANDARD

PRIORITY STATEMENT

This application is the national phase under 35 U.S.C. § 371 of PCT International Application No. PCT/SE2004/001813 which has an International filing date of Dec. 9, 2004, which designated the United States of America, and which claims priority on Swedish Patent Application No. SE 0303338-8, filed Dec. 11, 2003, the entire contents of which are hereby incorporated by reference.

BACKGROUND

1. Field

Example embodiments relate to an optical reference standard and in particular to an optical reference standard usable in the calibration of an optical analysis instrument.

2. Description of the Related Art

Optical reference standards are widely used in optical spectroscopy in order to ensure the correct performance of an analysis instrument. This is typically achieved through the comparison of measurements of optical properties of the optical reference standard performed on one instrument (so called 'slave' instrument) with similar measurements performed on the same optical reference standard by a reference instrument (so called 'master' instrument) of the same type. Moreover it is known to carry out similar comparative measurements between slave instruments or on the master instrument using the same optical reference standard for each measurement of the comparison.

When using a model, such as a regression model, derived either on the master instrument or using data from several instruments then the accuracy of the slave instrument in determining properties or constituents of a material to be analysed, such as a feed or foodstuff (including any starting or intermediate products), depends upon the accuracy with which the wavelengths and associated radiative intensities in a wavelength range particular to the material can be determined. In order to provide an accurate calibration of the instrument it is therefore important that the optical reference standard has optical characteristics in the wavelength range of interest that are close to the material to be analysed. It is also important in this respect that the reference standard has optical scattering characteristics similar to the material to be analysed.

Moreover, there are often large geographical distances between instruments and attendant time lags between measurements done on the master and the slave(s). A typical instrument standardisation involves making a standardisation measurement on the master instrument, transporting the results of this and the optical reference standard to the slave where the measurements are repeated, and finally transporting the reference standard back to the master where a confirmation measurement is done and a comparison is made with the original standardisation measurement in order to ensure the validity of any associated instrument standardisation. It is therefore also important that the optical reference standard has both mechanical and temporal stability sufficient for the optical properties of the standard to remain substantially constant (that is differences less than what are expected to occur between instruments), at least between measurements by the master.

It is known from U.S. Pat. No. 4,866,644 to provide a reference standard consisting of the particular feed or foodstuff to be analysed. Whilst, in the case of dry feed and foodstuffs, the so produced optical reference standard may have sufficient mechanical and temporal stability this is not the case for 'wet' feed and foodstuffs (i.e. solid products having a significant water or other edible-liquid content, such as vegetable oils, or fat content). Such wet products normally undergo rapid chemical changes and are mechanically relatively unstable. Thus, even with the careful and rapid transportation of optical reference standards consisting of such material, it is likely that changes will occur in its optical properties between measurements. This renders such optical reference standards essentially useless.

However, there presently exists a desire to provide an optical reference standard using such natural products so as to likewise provide an effective reference standard for wet feed and foodstuffs. Moreover, where analysis instruments are deployed in-line in a feed or foodstuff production process any contamination problems caused if the line becomes exposed to the optical reference standard may be significantly reduced if the standard comprises such natural components as are typically found in feed and food.

It is an aim of the present invention to provide an optical reference standard for wet products in which at least some of the problems associated with the known standards are alleviated.

Accordingly, there is provided an optical reference standard including an optical reference material, wherein the optical reference material may include a binder and a cereal formed into a matrix to fixedly hold an amount of water, the reference material being constituted with the binder, the cereal and the water present in amounts to provide the reference standard with desired spectral, mechanical and temporal characteristics. The matrix formed by one or both of the binder and the cereal, which in the present context includes mixtures of different cereal crops, can hold the water spatially fixed so as to provide a reference standard, particularly for wet feed or foodstuffs, having enhanced mechanical and temporal stability.

Preferably the cereal employed is one or more of the group wheat, barley, oats and maize. More preferably the cereal employed is oats as this has been discovered by the inventors to provide an optical reference standard having particularly good mechanical and temporal stability.

Usefully, the amount, the constituency and/or the composition of the cereal can be varied together with or independently of the liquid content so as to provide an optical reference standard having scattering and/or spectral response properties that closely match the product to be analysed using the analysis instrument. In this way a better calibration of the analysis instrument can be performed.

The binder employed can usefully be a gelling agent, such as gelatin, that can advantageously provide mechanical stability and throughout which can be dispersed some or all of the water to thereby hold it fixedly located.

BRIEF DESCRIPTION OF THE DRAWINGS

These and other advantages will become apparent from a consideration of the following description of a preferred embodiment that is made with reference to the accompanying figures, of which.

DETAILED DESCRIPTION OF EXAMPLE EMBODIMENTS

Figure 1:
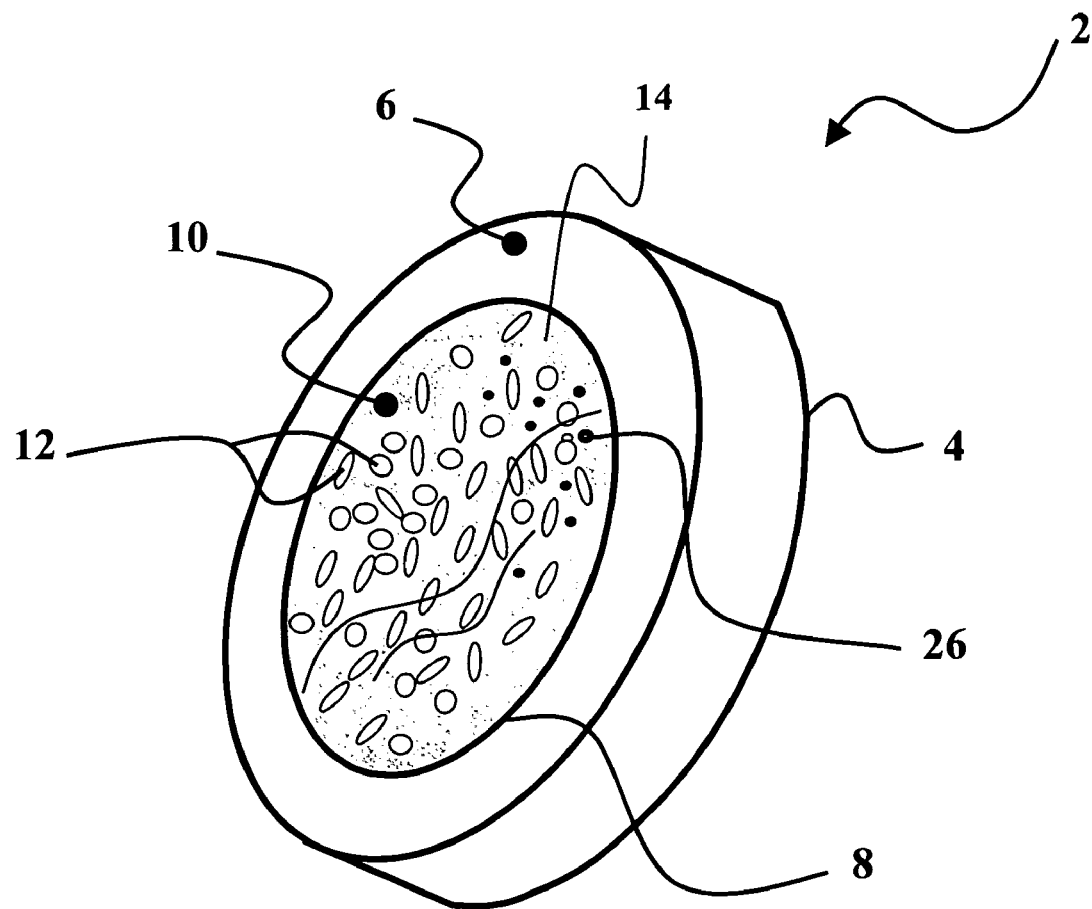
FIG. 1 shows schematically an optical reference standard according to the present invention.

Considering now FIG. 1, an exemplary embodiment of an optical reference standard 2 is illustrated and comprises a housing 4 having a surface 6, at least a portion of which comprises a window 8 of material transparent to the wavelengths of interest. When used in the calibration of a reflectance type optical instrument then this single window 8 will be sufficient. However, when the reference 2 is employed in the calibration of a transmission type optical instrument then a second window (not shown), usually located in a surface of the housing 4 opposing the surface 6, may be included. Indeed, it will be apparent to the person skilled in the art that the configuration and composition of windows in the housing may be non-inventively adapted depending on the nature of the optical instrument to be calibrated.

The housing 4 is filled with a reference material 10 composed to provide the desired optical properties, as is exemplified below. Generally the reference material 10 consists of a cereal 12 and binder 14 matrix by which is held, spatially fixed, a desired amount of the appropriate, preferably edible, liquid or liquids. The cereal 12 is illustrated as comprising coarse particles but may be ground to any degree and may consist of one or more cereal crop types, particularly so as to adapt the optical scattering properties of the optical reference standard 2.

A formulation of the reference material 10, particularly adapted to substantially match the optical properties of pulped sugar beet, will now be described by way of example only.

Pulped sugar beet largely consists of water, starch, sugars and some structural polysaccharides. The material is unstable both chemically and spectrally because crushing, cutting and/or pulping of the beet releases enzymes that rapidly start to break down the starch and sugar. In addition, oxidation also initiates changes. For these reasons beet pulp is not a suitable candidate as a standardisation medium. However there exists strong commercial drivers for the accurate and reproducible analysis of one or more quality parameters of sugar beet and hence there is a need for an optical reference by which to standardise slave instruments to match the response of a master instrument, employed to derive a sugar beet calibration.

In this example the reference material 10, consists of a mixture of gelatin binder 14 with oatmeal 12. The optical reference standard 2 formed using oatmeal has been found by the inventors to have good temporal and mechanical stability as well as suitable optical properties but barley and wheat or a mixture of some or all of these cereal crops can also be used to advantage.

A mixture of 20 g of gelatin in 100 ml of water was made up by adding the gelatin to heated water and allowing to cool. 30 g of oatmeal was added to 50 ml of the gelatin solution and blended using a mechanical food blender. This was allowed to cold set to form the reference material 10.

A relatively high concentration of oatmeal has been determined experimentally to provide a good match to the optical properties of the beet. Typically this concentration should be in the region of 20 to 30 g of oatmeal per 50 ml of the gelatin solution in order to match the absorption spectrum of sugar beet. Of course this concentration may be adjusted through experimental trials, comparing the spectral response of the standard 2, employing the material 10, with that of the target material. The concentration of gelatin in water can be likewise adapted to provide a required mechanical and temporal stability.

Figure 2:
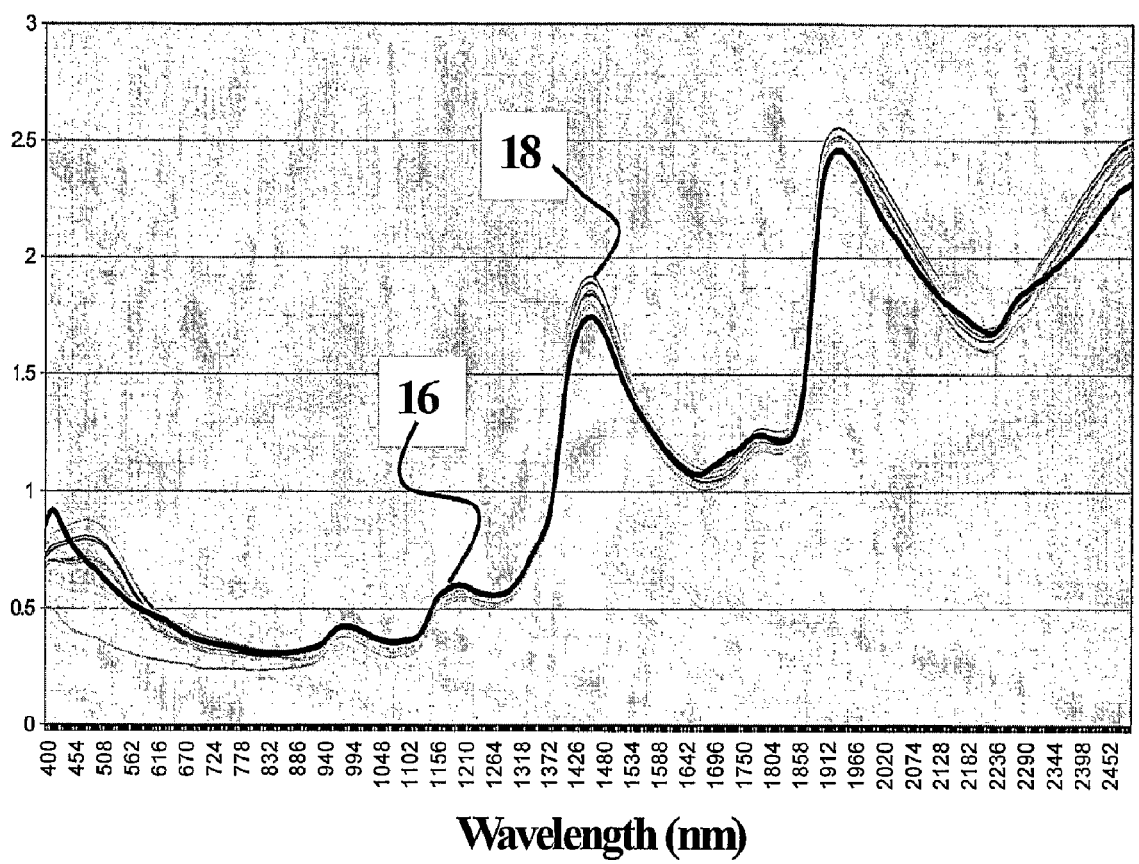
FIG. 2 shows a representative absorption spectrum of the standard of FIG. 1.

The optical absorption spectrum in a wavelength range of interest of the optical reference standard 2, formed using the optical reference material 10 is illustrated by a line 16 in FIG. 2. Spectra obtained from actual sugar beet samples in the same wavelength range are also illustrated in FIG. 2 by lines 18 that illustrate the typical intensity variations in the absorption spectra of different sugar beet samples.

Figure 3:
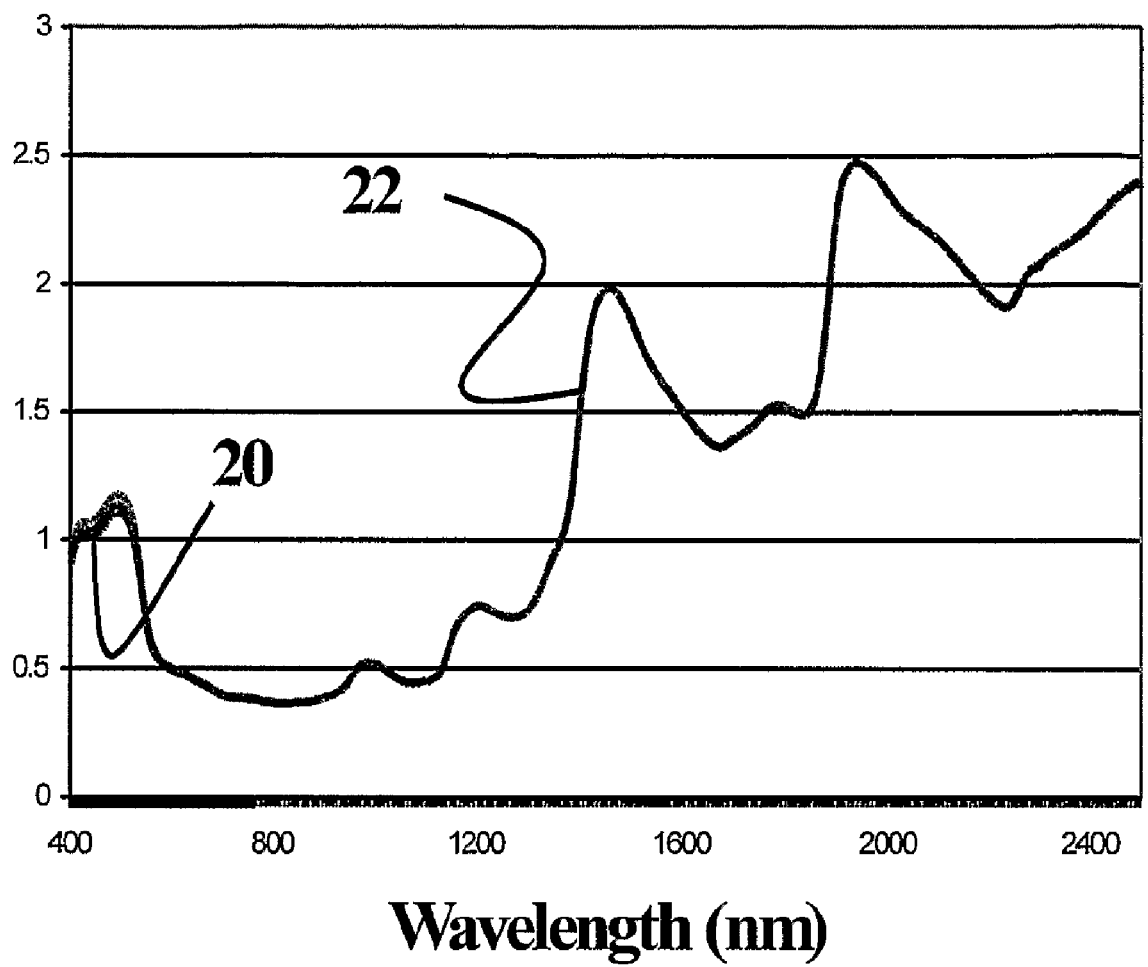
FIG. 3 is an illustration of the temporal stability of the spectral characteristics of the standard of FIG. 1.

The temporal stability of the reference standard 2 is illustrated in FIG. 3 in which spectra obtained from the same standard 2, using the same optical measurement instrument, some 16 days apart are show. A line 20 represents an initial spectrum that was obtained two days after the manufacture of the reference material 10 and a line 22 represents that spectrum obtained 16 days later. As can be seen by the person skilled in the art, the standard 2 is sufficiently stable spectrally for it to be employed as an optical reference standard.

Whilst the invention has been described with reference to oats other cereal crops, such as maize corn, rice, barley and wheat for example may substitute or be added. Other gelling agents, such as agar, starch, pectin and cellulose, that are capable of retaining liquid in a physically stable form may substitute for the gelatin without departing from the invention as claimed.

Moreover, other components may be added in order to achieve desired spectral properties of the standard; for example colouring agents (illustrated in FIG. 1 by particles (26)) such as carbon black, cellulose or a colouring (preferably edible) may be added to vary the optical density; starch or sugars may be added to achieve the desired spectral response; or other liquids, such as vegetable oils, may substitute for or be used in conjunction with water whilst remaining within the scope of the invention as claimed.

The invention claimed is:

1. An optical reference standard for the calibration of an analysis instrument, comprising:
    an optical reference material including a binder and a cereal formed into a matrix to fixedly hold an amount of water, the reference material being constituted with the binder, the cereal and the water present in amounts to provide the reference standard with spectral, mechanical and temporal characteristics to imitate those of a product to be analyzed by an analysis treatment.

2. An optical reference standard as claimed in claim 1 wherein the cereal is selected from the group of one or more of oats, barley and wheat.

3. An optical reference standard as claimed in claim 2 wherein the cereal is oats in the form of one or other of oatmeal and oat flour.

4. An optical reference standard as claimed in claim 1, wherein the binder is a gelling agent.

5. An optical reference standard as claimed in claim 1, wherein the optical reference material further comprises one or more components selected to vary its optical density.

* * * * *